US008697666B2

(12) United States Patent
Klinman et al.

(10) Patent No.: US 8,697,666 B2
(45) Date of Patent: Apr. 15, 2014

(54) ANTI-CANCER OLIGODEOXYNUCLEOTIDES

(75) Inventors: Dennis M. Klinman, Potomac, MD (US); Hidekazu Ikeuchi, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 222 days.

(21) Appl. No.: 13/243,841

(22) Filed: Sep. 23, 2011

(65) Prior Publication Data

US 2012/0016013 A1 Jan. 19, 2012

Related U.S. Application Data

(63) Continuation of application No. 12/630,315, filed on Dec. 3, 2009, now Pat. No. 8,053,422.

(60) Provisional application No. 61/119,998, filed on Dec. 4, 2008.

(51) Int. Cl.
*C12N 15/113* (2010.01)
*C07H 21/04* (2006.01)

(52) U.S. Cl.
USPC ........................................ 514/44 A; 536/23.1

(58) Field of Classification Search
None
See application file for complete search history.

(56) References Cited

U.S. PATENT DOCUMENTS

| 6,653,292 | B1 | 11/2003 | Krieg et al. |
| 7,087,586 | B2 | 8/2006 | Filion et al. |
| 7,119,078 | B2 | 10/2006 | Jing et al. |
| 7,358,068 | B2 | 4/2008 | Vaillant et al. |
| 2004/0132682 | A1 | 7/2004 | Klinman et al. |
| 2004/0248834 | A1 | 12/2004 | Klinman et al. |
| 2005/0239733 | A1 | 10/2005 | Jurk et al. |

FOREIGN PATENT DOCUMENTS

| WO | WO 03/027313 | 4/2003 |
| WO | WO 2006/135434 | 12/2006 |

OTHER PUBLICATIONS

Klinman et al., "Therapeutic potential of oligonucleotides expressing immunosuppressive TTAGGG motifs," *Ann NY Acad Sci* 1058:87-95, 2005.

Klinman et al., Lecture entitled "Synthetic oligonucleotides as modulations of inflammation," National Cancer Institute sponsored Symposium, Apr. 10-11, 2008; *J. Leuk. Biol.* 84:1-7 (uncorrected version released on-line Apr. 22, 2008).

Klinman, "Immunotherapeutic uses of CpG oligodeoxynucleotides," *Nat. Rev. Immun.*, 4:249-258, 2004.

Krieg, "Development of TLR9 agonists for cancer therapy," *J. Clin. Invest.* 117(5):1184-1194, 2007.

Merrell et al., "Toll-Like Receptor 9 Agonists Promote Cellular Invasion by Increasing Matrix Metalloproteinase Activity," *Molec. Cancer Res.* 10:1541-7786, 2006.

Peter et al., "Characterization of suppressive oligodeoxynucleotides that inhibit Toll-like receptor-9-mediated activation of innate immunity," *Immunology* 123:118-128, 2007.

Riou et al., "Cell senescence and telomere shortening induced by a new series of specific G-quadruplex DNA ligands," *Proc. Natl. Acad. Sci.* 99:2672-2677, 2002.

Sato et al., "Suppressive oligodeoxynucleotides inhibit silica-induced pulmonary inflammation," *J. Immunol.* 180(11):7648-7654, 2008.

Shirota et al., "Suppressive oligodeoxynucleotides inhibit Th1 differentiation by blocking IFN-gamma- and IL-12-mediated signaling," *J. Immunol.* 173(8):5002-5007, 2004.

Shirota et al., "Suppressive Oligodeoxynucleotides Protect Mice from Lethal Endotoxic Shock," *J. Immunol.* 174:4579-4583, 2005.

Yamada et al., "Effect of Suppressive DNA on CpG-Induced Immune Activation," *J. Immunol.* 169:5590-5594, 2002.

Yamada et al., "Suppressive oligodeoxynucleotides inhibit CpG-induced inflammation of the mouse lung," *Crit. Care Med.* 32(10):2045-2049, 2004.

*Primary Examiner* — Tracy Vivlemore
(74) *Attorney, Agent, or Firm* — Klarquist Sparkman, LLP

(57) ABSTRACT

It is disclosed herein that suppressive ODNs are of use for preventing or delaying the formation of a tumor, reducing the risk of developing a tumor, treating a tumor, preventing conversion of a benign to a malignant lesion, or preventing metastasis. In some embodiments, methods are disclosed herein for treating, preventing or reducing the risk of developing a tumor, such as esophageal, gastrointestinal, liver, lung, skin and colon tumors or a mesothelioma. Generally, the methods disclosed herein include selecting a subject for treatment and administering to the subject a therapeutically effective amount of one or more suppressive ODN. In some examples, additional agents can also be administered to the subject of interest.

20 Claims, 5 Drawing Sheets

ANTI-CANCER OLIGODEOXYNUCLEOTIDES

CROSS REFERENCE TO RELATED APPLICATIONS

This is a continuation of U.S. application Ser. No. 12/630,315, filed Dec. 3, 2009, issued as U.S. Pat. No. 8,053,422 on November 8, 2011 which claims the benefit of U.S. Provisional Application No. 61/119,998, filed Dec. 4, 2008, both of which are hereby incorporated by reference in their entirety.

FIELD OF THE DISCLOSURE

This relates to the field of cancer, specifically to nucleic acid molecules of use in preventing a tumor, delaying the development of a tumor, or reducing the risk of developing a tumor, such as skin cancer.

BACKGROUND

A majority of human cancers originate from epithelial tissue. A common cancer of epithelial origin is non-melanoma skin cancer (NMSC), including basal cell carcinoma (BCC) and squamous cell carcinoma (SCC), with more than 700,000 new cases diagnosed each year in the United States. Similar cancers are also seen in non-human animals such as domesticated animals and pets, including cats and dogs. BCC is rarely life-threatening because it is slow growing and is mostly localized. Unlike BCC, SCC metastasizes at a rate of 2% to 6% over several years after initial diagnosis. A highly malignant form invades and destroys tissue, and then metastasizes, initially to a regional lymph node before more distant organs such as the lung or brain are affected. SCC is commonly encountered in a number of epithelial tissues, including the oral cavity, esophagus, larynx, bronchi, intestines, colon, genital tract, and skin.

Murine skin model systems are still essential contributors to the understanding of the multi-step nature of chemically-induced carcinogenesis. In the multistage mouse skin carcinogenesis model, biochemical events unique to initiation, promotion, or progression can be studied and related to cancer formation. In that model, the NMSC that is most often induced is squamous cell carcinoma. Several protocols are used to develop mouse skin tumors in laboratory animals. In a common initiation-promotion protocol, mouse skin is treated with an initiating agent (7,12-dimethylbenz[a]anthracene; DMBA) and then with a potent tumor promoter (12-O-tetradecanoylphorbol-13-acetate; TPA). In this protocol, mice develop mostly benign papillomas, more than 90% of which regress after TPA treatment is stopped. Only a small percentage of papillomas progress to invasive SCC. This model system is routinely used to study skin cancer and agents that can treat and prevent skin cancer. However, a need remains for additional agents that can be used for the treatment and prevention of cancers, such as skin cancer.

SUMMARY OF THE DISCLOSURE

It is disclosed herein that suppressive ODNs are of use for preventing or delaying the formation of a tumor, reducing the risk of developing a tumor, treating a tumor, preventing conversion of a benign to a malignant lesion, or preventing metastasis.

In some embodiments, methods are disclosed herein for treating, preventing or reducing the risk of developing a tumor, including, but not limited to, esophageal, lung, gastrointestinal (such as stomach), liver, skin and colon tumors. The tumor can be benign or malignant. In one example, the cancer is a carcinoma. In another example, the tumor is a skin tumor, such as a melanoma or a basal cell carcinoma.

Generally, the methods disclosed herein include selecting a subject for treatment and administering to the subject a therapeutically effective amount of one or more suppressive ODN. In some examples, additional agents can also be administered to the subject of interest.

The foregoing and other features and advantages of the invention will become more apparent from the following detailed description of a several embodiments which proceeds with reference to the accompanying figures.

SEQUENCE LISTING

Figure 1:
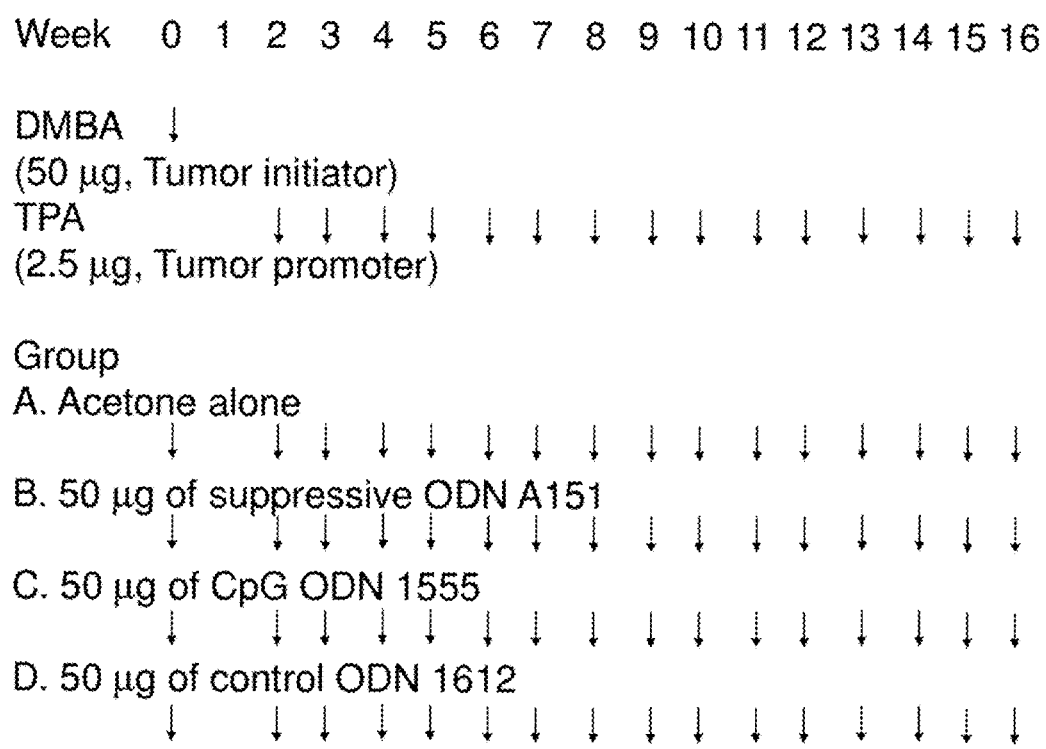
FIG. 1 is a schematic diagram of an exemplary protocol to test the effect of suppressive oligodeoxynucleotides (ODNs) on the formation of skin cancer in a mouse model system. Mice were treated with an initiator, 7,12-dimethylbenzathracene (DMBA) at the start of the experiment followed by treatment with a tumor promoter, phorbol 12-tetradecanoate 13-acetate (TPA) starting at week two at weekly intervals. ODNs were also administered starting at week two at weekly intervals. The ODNs tested include suppressive A151 (TTAGGGTTAGGG TTAGGGTTAGGG; SEQ ID NO: 1) and control ODN 1612 (GCTAGAGCTTAGGCT; SEQ ID NO: 29). TPA and ODN were CO-administered in acetone. Mice were treated in three experimental groups of 15 mice. Group A received DMBA and TPA; Group B received DMBA, TPA, and ODN A151; Group C received DMBA, TPA and ODN 1555; Group D received DMBA, TPA and ODN 1612.

The nucleic and amino acid sequences listed in the accompanying sequence listing are shown using standard letter abbreviations for nucleotide bases, and three letter code for amino acids, as defined in 37 C.F.R. 1.822. In the accompanying sequence listing:

SEQ ID NOs: 1-25 are the nucleic acid sequence of exemplary suppressive oligodeoxynucleotides.

SEQ ID NOs: 26-28 are inactive forms of suppressive oligodeoxynucleotides.

SEQ ID NO: 29 is the nucleic acid sequence of ODN 1612.

SEQ ID NO: 30 is the nucleic acid sequence of ODN 1555.

DETAILED DESCRIPTION OF SEVERAL EMBODIMENTS

I. Abbreviations

CD: Circular dichroism
DMBA: 7,12-dimethylbenz[a]anthracene
ODN: oligodeoxynucleotide
TPA: 12-O-tetradecanoylphorbol-13-acetate
UV: ultraviolet

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Actinic keratosis: A precancerous skin condition caused by overexposure to the sun. Actinic keratoses are small (usually less than one-fourth inch) rough spots that may be pink-red or flesh-colored. Usually they develop on sun-exposed areas of the skin, such as the face, ears, back of the hands, and arms, although they can arise on other sun-exposed areas of the skin. Actinic keratoses are slow growing. They usually do not cause any symptoms or signs other than patches on the skin. It is possible, but not common, for actinic keratoses to turn into squamous cell cancer. They also frequently go away on their own but return spontaneously.

Animal: Living multi-cellular vertebrate organisms, a category that includes, for example, mammals and birds. The term mammal includes both human and non-human mammals. Similarly, the term "subject" includes both human and veterinary subjects. Therefore, the general term "subject" is understood to include all animals, including, but not limited to, humans, or veterinary subjects, such as other primates, dogs, cats, horses, and cows.

Anti-inflammatory agent: Any of various medications that decrease the signs and symptoms (for example, pain, swelling, or shortness of breath) of inflammation. Corticosteroids are exemplary potent anti-inflammatory medications. Non-steroidal anti-inflammatory agents are also effective exemplary anti-inflammatory agents and do not have the side effects that can be associated with steroid medications.

CD value: The formation of G-tetrads yields a complex with different physical properties than the individual oligonucleotides. Spectroscopically, this is manifested by an increase in circular dichroism (CD), and an increase in peak absorbance to the 260-280 nm wavelength owing to the formation of secondary structures. In one embodiment, a method for identifying oligonucleotides that form G-tetrads is to assess the CD values. An increase in peak ellipticity values to greater than 2.0 is typical of a G-tetrad forming oligonucleotide; the higher the ellipticity value, the greater the tetrad-forming capacity of the oligonucleotide.

Chemokine: A type of cytokine (a soluble molecule that a cell produces to control reactions between other cells) that specifically alters the behavior of leukocytes (white blood cells). Examples include, but are not limited to, interleukin 8 (IL-8), platelet factor 4, and melanoma growth stimulatory protein.

Chemotherapeutic agent: An agent with therapeutic usefulness in the treatment of diseases characterized by abnormal cell growth (e.g., an anti-neoplastic agent). Such diseases include tumors, neoplasms, and cancer, as well as diseases characterized by hyperplastic growth such as psoriasis. In one embodiment, a chemotherapeutic agent is an agent of use in treating neoplasms such as solid tumors. Chemotherapeutic agents can be protein or non-protein agents, such as small molecule drugs, antibodies, peptides, proteins, and immunomodulators. In one embodiment, a chemotherapeutic agent is a radioactive molecule. One of skill in the art can readily identify a chemotherapeutic agent (for instance, see Slapak and Kufe, *Principles of Cancer Therapy*, Chapter 86 in *Harrison's Principles of Internal Medicine*, 14th edition; Perry et al., *Chemotherapy*, Ch. 17 in Abeloff, *Clinical Oncology* 2$^{nd}$ ed., © 2000 Churchill Livingstone, Inc; Baltzer L, Berkery R (eds): *Oncology Pocket Guide to Chemotherapy*, 2nd ed. St. Louis, Mosby-Year Book, 1995; Fischer D S, Knobf M F, Durivage H J (eds): *The Cancer Chemotherapy Handbook*, 4th ed. St. Louis, Mosby-Year Book, 1993).

Colon cancer: Colorectal cancer, also called large bowel cancer, includes cancerous growths in the colon, rectum and appendix. With 655,000 deaths worldwide per year, it is the third most common form of cancer and the second leading cause of cancer-related death in the Western world. Many colorectal cancers are thought to arise from adenomatous polyps in the colon. These mushroom-like growths are usually benign, but some may develop into cancer over time. The majority of the time, the diagnosis of localized colon cancer is through colonoscopy. Therapy is usually through surgery, which in many cases is followed by chemotherapy. The first symptoms of colon cancer are usually vague, such as bleeding, weight loss, and fatigue (tiredness). Local (bowel) symptoms are rare until the tumor has grown to a large size. Generally, the nearer the tumor is to the anus, the more bowel symptoms there will be.

Contacting: Placement in direct physical association, including both a solid and liquid form. Contacting can occur in vitro with isolated cells or in vivo by administering to a subject.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor α (TNFα), interleukin-6 (IL-6), interleukin-10 (IL-10), interleukin-12 (IL-12), macrophage inflammatory protein 2 (MIP-2), KC, and interferon-γ (INF-γ)

Decrease: Becoming less or smaller, as in number, amount, size, or intensity. In one example, decreasing the risk of a disease (such as for tumor formation) includes a decrease in the likelihood of developing the disease by at least about 20%, for example by at least about 30%, 40%, 50%, 60%, 70%, 80%, or 90%. In another example, decreasing the risk of a disease includes a delay in the development of the disease, for example a delay of at least about six months, such as about one year, such as about two years, about five years, or about ten years.

In one example, decreasing the signs and symptoms of a tumor includes decreasing the size, volume, or number of tumors (such as skin tumors) or metastases by a desired amount, for example by at least 5%, at least 10%, at least 15%, at least 20%, at least 25%, at least 30%, at least 50%, at least 75%, or even at least 90%, as compared to a response in the absence of the therapeutic composition.

Damaged DNA and DNA-damaging agents: Structural deviations in nucleoside-5'-monophosphates present in the genomic DNA of a eukaryotic cell. One type of structural deviation is a covalent joining of the adjacent pyrimidines through the formation of a cyclobutane ring structure at the C5 and C6 positions. Another type of structural deviation is an imidazole ring fragmentation of a purine (either adenine or guanine). The location of such structural deviations in a cell's genomic DNA is referred to as a "lesion." Damaged bases can arise from, for example, DNA-damaging agents, which include UV radiation, ionizing radiation, oxidative stress, alkylation damage or deamination. Examples of lesions include cis-syn and trans-syn II cyclobutane pyrimidine dimers, FapyA and FapyG (Lloyd, *Mutat. Res.* 408:159-170, 1998; Lloyd, *Progress in Nucleic Acid Research and Molecular Biology* 62:155-175, 1999). Alkylating agents are one form of DNA damaging agents.

Esophageal cancer: A malignancy of the esophagus. There are various subtypes, primarily squamous cell cancer and adenocarcinoma. Squamous cell cancer arises from the cells that line the upper part of the esophagus. Adenocarcinoma arises from glandular cells that are present at the junction of the esophagus and stomach. Esophageal tumors usually lead to dysphagia, pain and other symptoms, and are diagnosed with biopsy. Small and localized tumors are treated surgically with curative intent. Larger tumors tend not to be operable and hence cannot be cured; their growth can still be delayed with chemotherapy, radiotherapy or a combination of the two. In some cases chemo- and radiotherapy can render these larger tumors operable. Prognosis depends on the extent of the disease and other medical problems, but is fairly poor. Esophageal cancers are typically carcinomas which arise from the epithelium of the esophagus. Most esophageal cancers fall into one of two classes: squamous cell carcinomas, which are similar to head and neck cancer in their appearance and association with tobacco and alcohol consumption, and adenocarcinomas, which are often associated with a history of gastroesophageal reflux disease and Barrett's esophagus.

Enzyme: Any of numerous proteins or conjugated proteins produced by living organisms and functioning as biochemical catalysts.

Gastrointestinal cancer: Malignant conditions of the gastrointestinal tract, including the esophagus, stomach, liver, biliary system, pancreas, bowels, and anus. Many of these tumors are adenocarcinomas.

G-tetrad: G-tetrads are G-rich DNA segments that can accommodate complex secondary and/or tertiary structures. A G-tetrad involves the planar association of four Gs in a cyclic Hoogsteen hydrogen bonding arrangement (this involves non-Watson Crick base-pairing). In general, either a run of four or more contiguous Gs or a hexameric region in which >50% of the bases are Gs, is needed for an ODN to form a G-tetrad. The longer the run of contiguous Gs, and the higher the G content of the ODN, the higher the likelihood of G-tetrad formation, as reflected by higher CD or ellipticity values. Oligonucleotides that form G-tetrads can also form higher-level aggregates that are more easily recognized and taken up by immune cells, for example, through scavenger receptors or by nucleolin.

Guanosine-rich sequence: A nucleotide sequence in which 50% or more of the bases are Gs in a region of the oligonucleotide that it at least six nucleotides in length with an oligonucleotide. For example, in a hexamer, at least three nucleotides are Gs for a sequence to be guanosine rich. In an 11 nucleotide region or a 12 nucleotide region of an oligonucleotide, at least six nucleotides are Gs within that region of the oligonucleotide for that region to be guanosine rich. In one embodiment, a guanosine rich sequence is at least six nucleotides in length in an oligonucleotide of interest, such as an oligonucleotide of at least six to one hundred nucleotides in length or 15 to 50 nucleotides in length.

Immune response: A response of a cell of the immune system, such as a B cell or T cell to a stimulus. In one embodiment, the response is an inflammatory response.

Immunostimulatory CpG motifs: Immunostimulatory sequences that trigger macrophages, monocytes and lymphocytes to produce a variety of pro-inflammatory cytokines and chemokines. CpG motifs are found in bacterial DNA. The innate immune response elicited by CpG DNA reduces host susceptibility to infectious pathogens, and can also trigger detrimental inflammatory reactions. Immunostimulatory CpG motifs are found in "D" and "K" type ODNs (see, for example PCT Publication No. WO 01/51500, published on Jul. 19, 2001).

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Liver cancer: The most frequent, malignant, primary liver cancer is hepatocellular carcinoma. More rare primary forms of liver cancer include cholangiocarcinoma, mixed tumors, tumors of mesenchymal tissue, sarcoma and hepatoblastoma, a rare malignant tumor in children. Hepatocellular carcinoma is a primary malignancy (cancer) of the liver. Most cases of HCC are secondary to either a viral hepatitis infection (hepatitis B or C) or cirrhosis.

Macroscopically, liver cancer appears as a nodular or infiltrative tumor. The nodular type may be solitary (large mass) or multiple (when developed as a complication of cirrhosis). Tumor nodules are round to oval, grey or green (if the tumor produces bile), well circumscribed but not encapsulated. The diffuse type is poorly circumscribed and infiltrates the portal veins, or the hepatic veins (rarely).

Microscopically, there are four architectural and cytological types (patterns) of hepatocellular carcinoma: fibrolamellar, pseudoglandular (adenoid), pleomorphic (giant cell) and clear cell. In well differentiated forms, tumor cells resemble hepatocytes, form trabeculae, cords and nests, and may contain bile pigment in cytoplasm. In poorly differentiated forms, malignant epithelial cells are discohesive, pleomorphic, anaplastic, and giant. The tumor has a scant stroma and central necrosis because of the poor vascularization.

Treatment options of HCC and prognosis are dependent on many factors but especially on tumor size and staging. Tumor grade is also important. High-grade tumors will have a poor prognosis, while low-grade tumors may go unnoticed for many years, as is the case in many other organs, such as the breast, where a ductal carcinoma in situ (or a lobular carcinoma in situ) may be present without any clinical signs and without correlate on routine imaging tests, although in some occasions it may be detected on more specialized imaging studies like MR mammography (it should be stated, however, that the sensitivity of this technique remains, even with current state-of-the-art technology, below 50%). The usual outcome is poor, because only 10-20% of hepatocellular carcinomas can be removed completely using surgery.

Lung cancer: The main type of lung cancer is carcinoma of the lung, which includes small cell lung carcinoma and non-small cell lung carcinoma. Non-small cell lung carcinoma (NSCLC) is sometimes treated with surgery, while small cell lung carcinoma (SCLC) usually responds to chemotherapy and radiation. The most common cause of lung cancer is long-term exposure to tobacco smoke.

The non-small cell lung carcinomas are grouped together because their prognosis and management are similar. There are three main sub-types: squamous cell lung carcinoma, adenocarcinoma, and large cell lung carcinoma. Squamous cell lung carcinoma usually starts near a central bronchus. Cavitation and necrosis within the center of the cancer is a common finding. Well-differentiated squamous cell lung cancers often grow more slowly than other cancer types. Adenocarcinoma accounts for 29.4% of lung cancers. It usually originates in peripheral lung tissue. Most cases of adenocarcinoma are associated with smoking; however, among people who have never smoked, adenocarcinoma is the most common form of lung cancer. A subtype of adenocarcinoma, the bronchioloalveolar carcinoma, is more common in females.

Small cell lung cancers (SCLC, also called "oat cell carcinoma") is less common. It tends to arise in the larger airways (primary and secondary bronchi) and grows rapidly, becoming quite large. The "oat" cell contains dense neurosecretory granules (vesicles containing neuroendocrine hormones), which give this an endocrine/paraneoplastic syndrome association. While initially more sensitive to chemotherapy, it ultimately carries a worse prognosis and is often metastatic at presentation. Small cell lung cancers are divided into limited stage and extensive stage disease. This type of lung cancer also is strongly associated with smoking.

Malignant cells: Cells which have the properties of anaplasia, invasion and metastasis.

Melanoma: A form of cancer that originates in melanocytes (cells that make the pigment melanin). Melanocytes are found primarily in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism) which is a marker of aggressive behavior and a tendency to local recurrence. Other melanomas include clear cell sarcoma, mucosal melanoma and uveal melanoma.

Features that affect prognosis are tumor thickness in millimeters (Breslow's depth), depth related to skin structures (Clark level), type of melanoma, presence of ulceration, presence of lymphatic/perineural invasion, presence of tumor infiltrating lymphocytes (if present, prognosis is better), location of lesion, presence of satellite lesions, and presence of regional or distant metastasis. When melanomas have spread to the lymph nodes, one of the most important factors is the number of nodes with malignancy. The extent of malignancy within a node is also important; micrometastases in which malignancy is only microscopic have a more favorable prognosis than macrometastases. When there is distant metastasis, the five year survival rate is less than 10 percent; the median survival is 6 to 12 months. Metastases to skin and lungs have a better prognosis. Metastases to brain, bone and liver are associated with a worse prognosis.

Melanoma can be staged as follows:
Stage 0: Melanoma in situ (Clark Level I), 100% Survival
Stage I/II: Invasive Melanoma, 85-95% Survival
    T1a: Less than 1.00 mm primary, w/o Ulceration, Clark Level II-III
    T1b: Less than 1.00 mm primary, w/Ulceration or Clark Level IV-V
    T2a: 1.00-2.00 mm primary, w/o Ulceration
Stage II: High Risk Melanoma, 40-85% Survival
    T2b: 1.00-2.00 mm primary, w/ Ulceration
    T3a: 2.00-4.00 mm primary, w/o Ulceration
    T3b: 2.00-4.00 mm primary, w/ Ulceration
    T4a: 4.00 mm or greater primary w/o Ulceration
    T4b: 4.00 mm or greater primary w/ Ulceration
Stage III: Regional Metastasis, 25-60% Survival
    N1: Single Positive Lymph Node
    N2: 2-3 Positive Lymph Nodes OR Regional Skin/In-Transit Metastasis
    N3: 4 Positive Lymph Nodes OR Lymph Node and Regional Skin/In Transit Metastases
Stage IV: Distant Metastasis, 9-15% Survival
    M1a: Distant Skin Metastasis, Normal lactate dehydrogenase (LDH)
    M1b: Lung Metastasis, Normal LDH
    M1c: Other Distant Metastasis OR Any Distant Metastasis with Elevated LDH Mesothelioma: A form of cancer that is almost always caused by previous exposure to asbestos. In this disease, malignant cells develop in the mesothelium, a protective lining that covers most of the body's internal organs. The most common site is the pleura (outer lining of the lungs and internal chest wall), but it may also occur in the peritoneum, the heart, the pericardium or tunica vaginalis. Most people who develop mesothelioma have worked on jobs where they inhaled asbestos particles, or they have been exposed to asbestos dust and fiber in other ways.

The mesothelium consists of a single layer of flattened to cuboidal cells forming the epithelial lining of the serous cavities of the body including the peritoneal, pericardial and pleural cavities. It is believed that deposition of asbestos fibers in the parenchyma of the lung may result in the penetration of the visceral pleura from where the fiber can then be carried to the pleural surface, thus leading to the development of malignant mesothelial plaques.

Normal cells: Non-diseased (wild-type) cells, such as non-tumor, non-malignant cells.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (i.e., molecules comprising a sugar (e.g., ribose or deoxyribose) linked to a phosphate group and to an exchangeable organic base, which is either a substituted pyrimidine (Py) (e.g., cytosine (C), thymine (T) or uracil (U)) or a substituted purine (Pu) (e.g., adenine (A) or guanine (G)). The term "oligonucleotide" as used herein refers to both oligoribonucleotides and oligodeoxyribonucleotides (ODNs). The term "oligonucleotide" also includes oligonucleosides (i.e., an oligonucleotide minus the phosphate) and any other organic base polymer. Oligonucleotides can be obtained from existing nucleic acid sources (e.g., genomic or cDNA), but are preferably synthetic (i.e., produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "oligonucleotide delivery complex" is an oligonucleotide associated with (e.g., ionically or covalently bound to; or encapsulated within) a targeting means (e.g., a molecule that results in a higher affinity binding to a target cell (e.g., B-cell or natural killer (NK) cell) surface and/or increased cellular uptake by target cells). Examples of oligonucleotide delivery complexes include oligonucleotides associated with: a sterol (e.g., cholesterol), a lipid (e.g., cationic lipid, virosome or liposome), or a target cell specific binding agent (e.g., a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional (Gursel, *J. Immunol.* 167: 3324, 2001).

Papilloma: A benign tumor derived from epithelium. Papillomas may arise from skin, mucous membranes, or glandular ducts. Papillomas generally have a clear-cut border that projects above the surrounding tissue.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intraarticularly, or subcutaneously, and various surface applications including intranasal, intradermal, and topical application, for instance.

Pharmaceutical agent or drug: A chemical compound or composition capable of inducing a desired therapeutic or prophylactic effect when properly administered to a subject. Pharmaceutical agents include, but are not limited to, anti-infective agents, anti-inflammatory agents, bronchodilators, enzymes, expectorants, leukotriene antagonists, leukotriene formation inhibitors, and mast cell stabilizers.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the suppressive ODNs herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the development of a disease, such as a tumor, including preventing the conversion of a benign tumor to malignant cancer. "Treating" refers to a therapeutic intervention that ameliorates a sign or symptom of a disease or pathological condition after it has begun to develop. For example, "treating" a tumor can include reducing tumor volume, reducing the number of tumors or inhibiting metastasis of the tumor. "Ameliorating" refers to the reduction in the number or severity of signs or symptoms of a disease, such as cancer.

Squamous cell carcinoma: A type of cancer that originates in squamous cells, thin, flat cells that form the surface of the skin, eyes, various internal organs, and the lining of hollow organs and ducts of some glands. Squamous cell carcinoma is also referred to as epidermoid carcinoma. One type of squamous cell carcinoma is head and neck head squamous cell carcinoma (HNSCC). Head and neck squamous cell carcinoma includes cancers of the nasal cavity, sinuses, lips, mouth, salivary glands, throat and larynx.

HNSCC can be staged as follows:

Stage 0: No evidence of tumor.

Stage I: Tumor is 2 cm or less in greatest dimension; no evidence of regional lymph node involvement or distant metastasis.

Stage II: Tumor is more than 2 cm, but no larger than 4 cm; no evidence of regional lymph node involvement or distant metastasis.

Stage III: Tumor is larger than 4 cm; in some cases, the tumor has spread to the lymph nodes; no evidence of distant metastasis.

Stage IV: Tumor has spread to the lymph nodes; in some cases, distant metastases are present.

Subject at risk: An individual, such as a human or a veterinary subject, that is prone to developing s certain condition, such as a tumor. This can be due to their age, genotype, or due to an environmental exposure. Examples are a human subject who is exposed to a carcinogen due to an occupational exposure, or a human subject exposed to cigarette smoke, either because that individual smokes or due to exposure to second-hand smoke, or a subject exposed to ultraviolet light, such as due to tanning, or a subject genetically pre-disposed to developing a tumor.

Suppressive ODN: DNA molecules of at least eight nucleotides in length, such as about 8 to about 40 nucleotides in length or about ten to about 30 nucleotides in length, wherein the oligodeoxynucleotide has at least four guanosines, and has a CD value of greater than about 2.9 and suppresses an immune response in a subject, such as an immune response associated with the development of pneumoconiosis in a subject. Generally, a suppressive ODN has at least four guanosines. In additional embodiments, a suppressive ODN includes repeats of the nucleic acid sequence TTAGGG. Exemplary suppressive ODN are described below. In one embodiment, a suppressive ODN inhibits the generation of reactive oxygen intermediates, such as by macrophages.

Therapeutic agent: Used in a generic sense, it includes treating agents, prophylactic agents, and replacement agents.

Therapeutically effective amount: A quantity of a specified compound or ODN sufficient to achieve a desired effect in a subject being treated. For instance, this can be the amount of a suppressive ODN necessary to suppress CpG-induced immune cell activation in a subject, or a dose sufficient to prevent a tumor, delay the development of a tumor, or reduce the risk of developing a tumor. In one embodiment, a therapeutically effective amount of a suppressive ODN is the amount that alone, or together with one or more additional therapeutic agents (such antineoplastic agents or immunosuppressive agents), induces the desired response, such as prevention or treatment of a tumor, such as skin cancer. In other examples, it is an amount of an agent including one of the disclosed suppressive ODNs that can cause regression of an existing tumor, or treat one or more signs or symptoms associated with a tumor, in a subject. The preparations disclosed herein are administered in therapeutically effective amounts.

In one example, a desired response is to prevent the development of a tumor. In another example, a desired response is to delay the development, progression, or metastasis of a tumor, for example, by at least about 3 months, at least about six months, at least about one year, at least about two years, at least about five years, or at least about ten years. In a further example, a desired response is to decrease the occurrence of cancer, such as melanoma, colon cancer or lung cancer. In another example, a desired response is to decrease the signs and symptoms of cancer, such as the size, volume, or number of tumors or metastases. For example, the composition including a suppressive ODN can, in some examples, decrease the size, volume, or number of tumors (such as colorectal tumors) by a desired amount, for example by at least 5%, at least 10%, at least 15%, at least 20%, at least 25%, at least 30%, at least 50%, at least 75%, or even at least 90%, as compared to a response in the absence of the therapeutic composition.

The effective amount of a suppressive ODN that is administered to a human or veterinary subject will vary depending upon a number of factors associated with that subject, for example the overall health of the subject. An effective amount of an agent can be determined by varying the dosage of the product and measuring the resulting therapeutic response, such as the regression of a tumor. Effective amounts also can be determined through various in vitro, in vivo or in situ immunoassays. The disclosed agents can be administered in a single dose, or in several doses, as needed to obtain the desired response. However, the effective amount can be dependent on the source applied, the subject being treated, the severity and type of the condition being treated, and the manner of administration.

A therapeutically effective amount of a suppressive ODN can be administered systemically or locally. In addition, an effective amount of a suppressive ODN can be administered in a single dose, or in several doses, for example daily, during a course of treatment. However, the effective amount of the ODN will be dependent on the preparation applied, the subject being treated, the severity and type of the affliction, and the manner of administration of the compound. For example, a therapeutically effective amount of a suppressive ODN can vary from about 0.01 mg/kg body weight to about 1 g/kg body weight in some specific, non-limiting examples, or from about 0.01 mg/kg to about 60 mg/kg of body weight, based on efficacy.

The suppressive ODNs disclosed herein have equal applications in medical and veterinary settings. Therefore, the general term "subject" is understood to include all animals, including, but not limited to, humans or veterinary subjects, such as other primates, dogs, cats, horses, and cows.

Treatment: Refers to a therapeutic intervention that ameliorates a sign or symptom of a disease or pathological condition related to a disease (such as skin cancer, psoriasis or a tumor). Treatment can also induce remission or cure of such condition. In particular examples, treatment includes inhibiting a tumor, for example by inhibiting the full development of a tumor, such as preventing development of a metastasis or the development of a primary tumor, reducing tumor volume, or reducing the total number of tumors. Inhibition may not require a total absence of a tumor. In other examples, treatment includes inhibiting, reducing the risk of, or delaying development of, skin cancer. Reducing or suppressing a sign or symptom associated with a disease (such as a tumor, for example, skin cancer) can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having the disease), a reduction in the number of relapses of the disease, an improvement in the overall health or well-being of the subject, or by other parameters well known in the art that are specific to the particular disease.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma).

In several examples, a tumor is melanoma, esophageal cancer, liver cancer, gastrointestinal cancer, colon cancer or a lung carcinoma. In another example, a tumor is a skin tumor. In another example, a tumor is a papilloma.

Skin cancer is a malignant growth on the skin which can have many causes. Skin cancer generally develops in the epidermis (the outermost layer of skin), so a tumor is usually clearly visible. This makes most nonmelanoma skin cancers detectable in the early stages. Skin cancer represents the most commonly diagnosed malignancy, surpassing lung, breast, colorectal and prostate cancer.

The most common type of skin cancer is nonmelanoma skin cancer. Nonmelanoma skin cancers include all skin cancers except malignant melanoma (cancer that develops from melanocytes, the pigment-producing cells of the skin). There are many types of nonmelanoma skin cancers. Two common types of nonmelanoma skin cancer are basal cell carcinoma and squamous cell carcinoma. These two types of skin cancer are also known as keratinocyte carcinomas.

Basal cell carcinoma begins in the lowest layer of the epidermis, called the basal cell layer. About 70% to 80% of all skin cancers in men and 80% to 90% in women are basal cell carcinomas. They usually develop on sun-exposed areas, especially the head and neck. Basal cell carcinoma is slow growing. It is highly unusual for a basal cell cancer to spread to lymph nodes or to distant parts of the body. However, if a basal cell cancer is left untreated, it can grow into nearby areas and invade the bone or other tissues beneath the skin. After treatment, basal cell carcinoma can recur in the same place on the skin. Also, new basal cell cancers can start elsewhere on the skin. Within 5 years of being diagnosed with one basal cell cancer, 35% to 50% of people develop a new skin cancer.

Squamous cell carcinomas account for about 10% to 30% of all skin cancers. They commonly appear on sun-exposed areas of the body such as the face, ear, neck, lip, and back of the hands. Squamous cell carcinomas can also develop in scars or skin ulcers elsewhere. These carcinomas are generally more aggressive than basal cell cancers. Squamous cell carcinomas can sometimes start in actinic keratoses. Squamous cell carcinoma in situ (also called Bowen disease) is the earliest form of squamous cell skin cancer and involves cells that are within the epidermis and have not invaded the dermis.

Less common types of nonmelanoma skin cancer include Kaposi sarcoma, cutaneous lymphoma, skin adnexal tumors and various types of sarcomas and Merkel cell carcinoma. Together, these types of nonmelanoma skin cancer account for less than 1% of nonmelanoma skin cancers.

The most lethal type of skin cancer is melanoma. Melanoma (also known as malignant melanoma or cutaneous melanoma) is a cancer that begins in the melanocytes. Because most melanoma cells still produce melanin, melanoma tumors are usually brown or black. This form of skin cancer can be fatal if not treated early.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Description of Several Embodiments

A. Suppressive Oligodeoxynucleotides and Guanosine-Quadruplexes (G-Tetrads)

The present disclosure relates to the use of a class of DNA motifs that selectively inhibits or suppresses immune activation. Optimal activity is observed using multimers of these motifs, which are rich in G bases. The suppressive ODNs of the disclosure are highly specific (i.e., are neither toxic nor non-specifically immunosuppressive) with a good therapeutic index, and are useful for inhibiting an immune response. In one embodiment, a therapeutically effective amount of a suppressive ODN is of use for treating, delaying, preventing, or reducing the risk of developing a tumor. In some embodiments, the tumor is a skin, lung, gastrointestinal, liver, esophagus or colon tumor. In other embodiments a suppressive ODN is of use for preventing mesotheliomas. In a further embodiment, a suppressive ODN is of use for inhibiting or treating skin cancer, such as melanoma, squamous cell carcinoma, basal cell carcinoma, or keratinocyte carcinomas. In yet another embodiment, a suppressive ODN is of use for delaying, preventing, or reducing the risk of developing stomach cancer. The subject can have an inflammatory disorder that predisposes them to increased risk of cancer, such as colitis.

In some embodiments, the ODNs of use in the methods disclosed herein are capable of forming G-quadruplexes (G-tetrads). G-tetrads are G-rich DNA segments that can accommodate complex secondary and/or tertiary structures (see FIG. 1 of U.S. Patent Publication No. US-2004-0132682-A1, herein incorporated by reference). A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of continuous Gs, and the higher the G content of the ODN, the higher the likelihood of G-tetrad formation, as reflected by higher ellipticity values. Oligonucleotides that form G-tetrads can also form higher-level aggregates that are more easily recognized and taken up by immune cells, for example, through scavenger receptors or by nucleolin.

The CD value is an increase in peak absorbance to the 260-280 nm wavelength, generally owing to the formation of secondary structures. Thus, a convenient method for identifying suppressive oligonucleotides is to study their CD values. An increase in peak ellipticity values to greater than 2.0 is typical of a suppressive oligonucleotide, such as an ODN with at least four guanosines.

In some embodiments, suppressive ODNs can have CD values of about 2.2, 2.4, 2.6, 2.8, 3.0, 3.2, 3.5, 4.0, 4.5, 5.0, 5.5, 6.0, 6.5, 7.0, 7.5, 8.0, 8.5, 9.0, or higher. The higher the ellipticity value, the greater the tetrad-forming capacity of the oligonucleotide, so an ODN with a CD value of 8.5 is typically more suppressive than an ODN with a CD value of 2.9. Generally, a suppressive ODN includes at least four guanosines. In some embodiments, the ODN forms a G-tetrad.

In some embodiments, the ODN is from about 8 to about 100 nucleotides in length. In particular examples, the ODN is from about 8 to about 40 nucleotides in length, or from about 10 to about 30 nucleotides in length such as 18, 20, 22, 24, 26, or 28 nucleotides in length. Optionally, the suppressive ODN has multiple guanosine-rich sequences, for example, in certain embodiments the ODN has from about two to about 20 guanosine-rich sequences, or, more particularly, from about two to about four guanosine-rich sequences. In some embodiments, the suppressive ODN is 18, 24 or 30 nucleotides in length.

In one embodiment, the suppressive ODNs have a sequence comprising at least one of the human telomere-derived TTAGGG suppressive motifs. In some examples, the ODN has at least one TTAGGG motif, and in certain examples, the ODN has multiple TTAGGG motifs. For example, in particular embodiments, the ODN has from about two to about 20 TTAGGG motifs. In this context, "about" refers to a difference of an integer amount. Thus, in some examples, the suppressive ODNs have from two to five TTAGGG motifs, such as three or four TTAGGG motifs. In some embodiments, the ODN includes or consists of three, four, five, six, seven, eight, nine, ten, eleven, twelve, thirteen, fourteen or fifteen TTAGGG motifs. Single TTAGGG motifs are suppressive only when incorporated into larger ODNs with greater than 10 bases. In several examples, the suppressive ODN is from about 18 to about 30 nucleotides in length and includes three or four TTAGGG motifs.

Suppression of tumor formation can be induced by an ODN that includes a G-tetrad-forming sequence that imposes the two-dimensional structure necessary for G-tetrad formation. Examples of suppressive ODN include, but are not limited to, those shown in Table 1. However, any oligonucleotide capable of forming G-tetrads may be used to suppress tumor formation. In particular examples, the ODN comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25 (see Table 1). In some examples, the ODN consists a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25 (see Table 1).

Combinations of these ODNs are also of use in the methods disclosed herein. Thus, two, three, four, five, six, seven, eight, nine or more than ten of the oligodeoxynucleotides can be administered to a subject. These ODNs can be administered as parts of a single nucleotide molecule, or on different nucleotide molecules.

TABLE 1

Examples of suppressive ODNs

| | | | |
|---|---|---|---|
| 1 | A151 | SEQ ID NO: 1 | (TTAGGG)₄ (i.e.-4 repeats of the TTAGGG base sequence) |
| 2 | A152 | SEQ ID NO: 2 | (TTAGGG)₃ |
| 3 | A153 | SEQ ID NO: 3 | (TTAGGG)₂ |
| 4 | A156 | SEQ ID NO: 5 | (TGGGCGGT)₃ |
| 5 | A157 | SEQ ID NO: 5 | (TGGGCGGT)₂ |
| 6 | A1 | SEQ ID NO: 6 | TCAACCTTCATTAGGG |
| 7 | A161 | SEQ ID NO: 7 | TTAGGGTTAGGGTCAACCTTCA |
| 8 | A162 | SEQ ID NO: 8 | TCAACCTTCATTAGGGTTAGGG |
| 9 | A163 | SEQ ID NO: 9 | GGGTTAGGGTTATCAACCTTCA |
| 10 | A164 | SEQ ID NO: 10 | TCAACCTTCAGGGTTAGGGTTA |
| 11 | A15 | SEQ ID NO: 11 | GGGTGGGTGGGTATTACCATTA |
| 12 | A16 | SEQ ID NO: 12 | ATTACCATTAGGGTGGGTGGGT |
| 13 | A17 | SEQ ID NO: 13 | TGGGCGGTTCAAGCTTGA |
| 14 | A18 | SEQ ID NO: 14 | TCAAGCTTCATGGGCGGT |
| 15 | A19 | SEQ ID NO: 15 | GGGTGGGTGGGTAGACGTTACC |
| 16 | A20 | SEQ ID NO: 16 | GGGGGGTCAAGCTTCA |
| 17 | A21 | SEQ ID NO: 17 | TCAAGCTTCAGGGGGG |
| 18 | A22 | SEQ ID NO: 18 | GGGGGGTCAACGTTCA |
| 19 | H154 | SEQ ID NO: 19 | CCTCAAGCTTGAGGGG |
| 20 | 1502 | SEQ ID NO: 20 | GAGCAAGCTGGACCTTCCAT |
| 21 | 1502(7DG) | SEQ ID NO: 26 | GAGCAAGCTG*G*ACCTTCCAT |
| 22 | 1502-1555 | SEQ ID NO: 21 | GAGCAAGCTGGTAGACGTTAG |
| 23 | 1502-1555(7DG) | SEQ ID NO: 27 | GAG*CAAGCTG*GTAGACGTTAG |
| 24 | 1502-1555(7DG) | SEQ ID NO: 28 | G*AGCAAGCTG*GTAGACGTTAG |
| 25 | 1503 | SEQ ID NO: 22 | GGGCAAGCTGGACCTGGGGG |
| 26 | 1504 | SEQ ID NO: 23 | GGGGAAGCTGGACCTGGGGG |
| 27 | 1505 | SEQ ID NO: 24 | GGGCAAGCTGGACCTTCGGG |
| 28 | 1506 | SEQ ID NO: 25 | GGCAAGCTGGACCTTCGGGGGG |

In the table above, G* indicates 7-deazaguanine. Due to the presence of 7-deazaguanine, ODN 21 (SEQ ID NO: 26) is an inactive form of ODN 20 (SEQ ID NO: 20), and ODNs 1502-1555 (7DG) (SEQ ID NOs: 27 and 28) are inactive forms of ODN 1502-1555 (SEQ ID NO: 21).

Furthermore, in particular embodiments, the ODN is modified to prevent degradation. In one embodiment, suppressive ODNs can include modified nucleotides to confer resistance to degradation. Without being bound by theory, modified nucleotides can be included to increase the stability of a suppressive ODN. Thus, because phosphorothioate-modified nucleotides confer resistance to exonuclease digestion, the suppressive ODNs are "stabilized" by incorporating phosphorothioate-modified nucleotides.

In some embodiments, the ODN has a phosphate backbone modification, and in particular examples, the phosphate backbone modification is a phosphorothioate backbone modification. In one embodiment, the guanosine-rich sequence and its immediate flanking regions include phosphodiester rather than phosphorothioate nucleotides. In one specific non-limiting example, the sequence TTAGGG includes phosphodiester bases. In some examples, all of the bases in an ODN are phosphodiester bases. In other examples, the ODN is a phosphorothioate/phosphodiester chimera.

As disclosed herein, any suitable modification can be used to render the ODN resistant to degradation in vivo (such as resistant to degradation by an exo- or endo-nuclease). In one specific, non-limiting example, a modification that renders the ODN less susceptible to degradation is the inclusion of nontraditional bases such as inosine and queuosine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

The suppressive ODNs of the disclosure can be synthesized by standard methods well known in the art. Most commonly, synthesis is performed on an oligonucleotide synthesizer using the standard cyanoethyl phosphoramidite chemistry. These include, but are not limited to, phosphodiester, phosphorothioate, peptide nucleic acids, synthetic peptide analogues, and any combination thereof. Those skilled in the art will recognize that any other standard technique may be used to synthesize the suppressive ODN described herein.

In one embodiment, a suppressive ODN is included in a delivery complex. The delivery complex can include the suppressive ODN and a targeting agent. Any suitable targeting agent can be used. For example, in some embodiments, a suppressive ODN is associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). Examples of ODN delivery complexes include a suppressive ODN associated with a sterol (e.g., cholesterol), a lipid (e.g., a cationic lipid, anionic lipid, virosome or liposome), and a target cell specific binding agent (e.g., a ligand recognized by target cell specific receptor). Without being bound by theory, the complex is sufficiently stable in vivo to prevent significant uncoupling prior to delivery to the target cell. In one embodiment, the delivery complex is cleavable such that the ODN is released in a functional form at the target cells.

B. Pharmaceutical Compositions and Methods of Use

Methods are disclosed herein for preventing formation of a tumor, treating a tumor, or reducing the risk of developing a tumor. In some embodiments, methods are disclosed herein for preventing conversion of a benign to a malignant lesion, or preventing metastasis. The tumor can be any tumor, including, but not limited to, tumors of the esophagus, lung, liver, skin and colon and gastrointestinal tract. In some examples, the tumor can be a mesothelioma or stomach cancer. In other examples, the tumor is a skin tumor, such as, but not limited to, a squamous cell carcinoma or a basal cell carcinoma. The tumor can be benign or malignant. In some examples, the benign tumor is a papilloma. In some embodiments, the tumor or cancer is an inflammatory tumor or cancer. In other embodiments, the tumor or cancer is a non-inflammatory tumor or cancer.

The methods disclosed herein include selecting a subject in need of treatment for the condition (for example, a subject with a tumor or a subject at risk of developing a tumor, such as subject exposed to a carcinogen), and administering to the subject a therapeutically effective amount of one or more suppressive ODN. Additional agents can also be administered to the subject of interest.

In several embodiments, the present disclosure is further directed to methods for decreasing the risk of developing a tumor in a subject exposed to a carcinogen, or preventing or delaying the development of a tumor. The tumor can be skin cancer, such as basal cell carcinoma, keratinocyte carcinomas or a squamous cell carcinoma. The tumor can also be an esophageal, stomach, lung or colon tumor. In other embodiments a suppressive ODN is of use for preventing mesotheliomas. In a further embodiment, a suppressive ODN is of use for inhibiting skin cancer, such as melanoma, squamous cell carcinoma, basal cell carcinoma, or keratinocyte carcinomas. In some examples, the skin tumor is a papilloma.

Treatment of the conditions described herein can be prophylactic or, alternatively, can be initiated after the development of a condition described herein. Treatment that is prophylactic, for instance, can be initiated before a subject manifests symptoms of a condition. In some examples, such as for skin cancer, treatment can be initiated before or during exposure to an agent that damages DNA, such as a result of an exposure to a carcinogen or UV light, oxidative stress, alkylation damage and deamination. In some examples, treatment can be following the exposure to the DNA damaging agent, but before the appearance of a tumor. In some examples, treatment can be before or during exposure to a carcinogen, such as an occupational exposure, such as to asbestos, or smoking. Treatment prior to the development of the condition is referred to herein as treatment of a subject that is "at risk" of developing the condition. Accordingly, administration of a composition can be performed before, during, or after the occurrence of the conditions described herein.

Treatment initiated after the development of a condition may result in decreasing the severity of the symptoms of one of the conditions, or completely removing the symptoms, or reducing metastasis, tumor volume or number of tumors.

Non-limiting examples of subjects particularly suited to receiving the composition are those who may be exposed to natural or artificial UV irradiation, subjects who are exposed to a carcinogen due to an occupational exposure to an industrial chemical, or due to smoking, exposure to a viral infection, or exposure to a virus that induces or promotes tumor development (such as a papilloma). The subject can be exposed to asbestos or silica, and thus be at risk for mesothelioma. In some examples, these subjects have not yet developed tumors. In other examples, these subjects have a benign tumor that can convert into a malignant or even metastatic lesion. Examples of subjects suited to treatment are smokers who have not developed lung cancer. Examples of subjects suited to treatment also are those exposed to large amounts of UV light, but who have not developed skin cancer, such as a melanoma or a basal cell carcinoma. Additional examples of subjects suited to treatment are those subjects who have an occupational exposure to a carcinogen, such as asbestos.

In this aspect of the disclosure, the formation of tumors are delayed, prevented or decreased. The types of tumors that may occur in response to an agent that damages DNA in the skin include actinic keratosis, basal cell carcinoma, squamous cell carcinoma, and melanoma.

The method includes treating a subject of interest, such as a subject exposed to a DNA damaging agent, with a composition that includes an effective amount of a suppressive ODN. Whether the formation of tumors in an animal is reduced can be determined by the use of animal models, for instance mice that have been exposed to solar-simulated light or exposure to sunlight, using the models wherein an animal is exposed to a DNA alkylating agent, or using a model described in the examples section. Solar-simulated light is light having a spectral profile which is similar to natural solar irradiation, i.e. the emission spectrum of a solar simulator looks similar to spectrum of a solar noon day. Wavelengths of light include ~295-400 nm so is inclusive of UVA, UVB but not UVC which does not penetratethe ozone layer of the atmosphere (see, for instance, Yoon et al., *J. Mol. Biol.* 299: 681-693, 2000). However, the methods are of use with any initiating agent, including agents known to cause cancer (such as the carcinogens in tobacco smoke). In some embodiments, the subject is at risk of exposure to an initiating agent due to an occupational exposure.

The presence of a tumor can be determined by methods known in the art, and typically include cytological and morphological evaluation. The cells can be in vivo or ex vivo, including cells obtained from a biopsy.

The suppressive ODNs described herein may be formulated in a variety of ways for administration to a subject to delay, prevent, reduce the risk of developing, or treat, any tumor of interest. The suppressive ODNs described herein can also be formulated for application such that they prevent metastasis of an initial lesion.

The ODN also can be administered to slow or inhibit the growth of cells, such as cancer cells, or to inhibit the conversion of a benign lesion to a malignant one. In these applications, a therapeutically effective amount of a suppressive ODN is administered to a subject in an amount sufficient to inhibit growth, replication or metastasis of cancer cells, or to inhibit a sign or a symptom of the cancer. In some embodiments, the suppressive ODN are administered to a subject to inhibit or prevent the development of metastasis, or to decrease the number of micrometastases, such as micrometastases to the regional lymph nodes (Goto et al., *Clin. Cancer Res.* 14(11):3401-3407, 2008).

Pharmaceutical compositions can include at least one suppressive ODN as described herein as an active ingredient, or include both a suppressive ODN and an additional agent, such as an additional anti-inflammatory, UV protectant or an additional chemotherapeutic agent.

Pharmaceutical compositions are thus provided for both local (such as topical or inhalational) use and for systemic (such as oral or intravenous) use. Therefore, the disclosure includes within its scope pharmaceutical compositions comprising at least one suppressive ODN formulated for use in human or veterinary medicine. While the suppressive ODNs will typically be used to treat human subjects they may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen.

In one embodiment, a therapeutically effective amount of a suppressive ODN is formulated for administration to the skin. Formulations suitable for topical administration can include dusting powders, ointments, creams, gels or sprays for the administration of the active compound to cells, such as skin cells. Such formulations may optionally include an inorganic pigment, organic pigment, inorganic powder, organic powder, hydrocarbon, silicone, ester, triglyceride, lanolin, wax, cere, animal or vegetable oil, surfactant, polyhydric alcohol, sugar, vitamin, amino acid, antioxidant, free radical scavenger, ultraviolet light blocker, sunscreen agents, preservative, fragrance, thickener, or combinations thereof.

As one example, the active compounds of the present disclosure can be used in cosmetic formulations (e.g., skincare cream, sunscreen, decorative make-up products, and other dermatological compositions) in various pharmaceutical dosage forms, and especially in the form of oil-in-water or water-in-oil emulsions, solutions, gels, or vesicular dispersions. The cosmetic formulations may take the form of a cream which can be applied either to the face or to the scalp and hair, as well as to the human body, in particular those portions of the body that are chronically exposed to sun. They can also serve as a base for a lipstick.

In some cosmetic formulations, additives can be included such as, for example, preservatives, bactericides, perfumes, antifoams, dyes, pigments which have a coloring action, surfactants, thickeners, suspending agents, fillers, moisturizers, humectants, fats, oils, waxes or other customary constituents of a cosmetic formulation, such as alcohols, polyols, polymers, foam stabilizers, electrolytes, organic solvents, or silicone derivatives.

Cosmetic formulations typically include a lipid phase and often an aqueous phase. The lipid phase can be chosen from the following group of substances: mineral oils, mineral waxes, such as triglycerides of capric or of caprylic acid, castor oil; fats, waxes and other natural and synthetic fatty substances, esters of fatty acids with alcohols of low C number, for example with isopropanol, propylene glycol or glycerol, or esters of fatty alcohols with alkanoic acids of low C number or with fatty acids; alkyl benzoates; silicone oils, such as dimethylpolysiloxanes, diethylpolysiloxanes, diphenylpolysiloxanes and mixed forms thereof.

If appropriate, the aqueous phase of the formulations according to the present disclosure include alcohols, diols or polyols of low C number and ethers thereof, such as ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, such as silicon dioxide, aluminium silicates, polysaccharides and derivatives thereof, for example hyaluronic acid, xanthan gum and hydroxypropyl-methylcellulose, or poly-acrylates.

An exemplary cosmetic formulation is as an additive to a sunscreen composition as a lotion, spray or gel, for administration to the skin. A sunscreen can additionally include at least one further UVA filter and/or at least one further UVB filter and/or at least one inorganic pigment, such as an inorganic micropigment. The UVB filters can be oil-soluble or water-soluble. Oil-soluble UVB filter substances can include, for example: 3-benzylidenecamphor derivatives, such as 3-(4-methylbenzylidene) camphor and 3-benzylidenecamphor; 4-aminobenzoic acid derivatives, such as 2-ethylhexyl 4-(dimethylamino)benzoate and amyl 4-(dimethylamino) benzoate; esters of cinnamic acid, such as 2-ethylhexyl 4-methoxycinnamate and isopentyl 4-methoxycinnamate; derivatives of benzophenone, such as 2-hydroxy-4-methoxy-benzophenone, 2-hydroxy-4-methoxy-4'-methylbenzophenone and 2,2'-dihydroxy-4-methoxybenzophenone; esters of benzalmalonic acid, such as di(2-ethylhexyl)-4-methoxybenzalmalonate. Water-soluble UVB filter substances can include the following: salts of 2-phenylbenzimidazole-5-sulphonic acid, such as its sodium, potassium or its triethanolammonium salt, and the sulphonic acid itself; sulphonic acid derivatives of benzophenones, such as 2-hydroxy-4-methoxybenzophenone-5-sulphonic acid and salts thereof; sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)benzenesulphonic acid and salts thereof. The list of further UVB filters mentioned which can be used in combination with the active agent(s) according to the disclosure is not intended to be limiting.

For treatment of the skin, a therapeutically effective amount of at least one immunosuppressive ODN also can be locally administered to only an affected area of the skin, such as in the form of an ointment. In one embodiment, the ointment is an entirely homogenous semi-solid external agent with a firmness appropriate for easy application to the skin. Such an ointment can include fats, fatty oils, lanoline, Vaseline, paraffin, wax, hard ointments, resins, plastics, glycols, higher alcohols, glycerol, water or emulsifier and a suspending agent. Using these ingredients as a base, a decoy compound can be evenly mixed. Depending on the base, the mixture can be in the form of an oleaginous ointment, an emulsified ointment, or a water-soluble ointment. Oleaginous ointments use bases such as plant and animal oils and fats, wax, Vaseline and liquid paraffin. Emulsified ointments are comprised of an oleaginous substance and water, emulsified with an emulsifier. They can take either an oil-in-water form (O/W) or a water-in-oil-form (W/O). The oil-in-water form (O/W) can be a hydrophilic ointment. The water-in-oil form (W/O) initially lacks an aqueous phase and can include hydrophilic Vaseline and purified lanoline, or it can contain a water-absorption ointment (including an aqueous phase) and hydrated lanoline. A water-soluble ointment can contain a completely water-soluble Macrogol base as its main ingredient.

Pharmaceutically acceptable carriers include a petroleum jelly, such as VASELINE®, wherein the petroleum jelly contains 5% stearyl alcohol, or petroleum jelly alone, or petroleum jelly containing liquid paraffin. Such carriers enable pharmaceutical compositions to be prescribed in forms appropriate for consumption, such as tablets, pills, sugar-coated agents, capsules, liquid preparations, gels, ointments, syrups, slurries, and suspensions. When locally administered into cells in an affected area or a tissue of interest, the at least one suppressive ODN can be administered in a composition that contains a synthetic or natural hydrophilic polymer as the carrier. Examples of such polymers include hydroxypropyl cellulose and polyethylene glycol. One or more suppressive ODN can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used. A therapeutically effective amount of one or more suppressive can also be incorporated into bandages.

The suppressive ODN can be formulated for administration by inhalation, such as, but not limited to, formulations for the treatment of lung or esophageal cancer. Inhalational preparations include aerosols, particulates, and the like. In general, the goal for particle size for inhalation is about 1 μm or less in order that the pharmaceutical reach the alveolar region of the lung for absorption. However, the particle size can be modified to adjust the region of disposition in the lung. Thus, larger particles can be utilized (such as about 1 to about 5 μm in diameter) to achieve deposition in the respiratory bronchioles and air spaces. In addition, oral formulations may be liquid (e.g., syrups, solutions, or suspensions), or solid (e.g., powders, pills, tablets, or capsules).

For administration by inhalation, the compounds can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

The compositions or pharmaceutical compositions also can be administered by any route, including parenteral administration, for example, intravenous, intraperitoneal, intramuscular, intraperitoneal, intrasternal, or intraarticular injection or infusion, or by sublingual, oral, topical, intranasal, or transmucosal administration, or by pulmonary inhalation. When suppressive ODNs are provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

Suppressive ODNs are also suitably administered by sustained-release systems. Suitable examples of sustained-release suppressive ODNs include suitable polymeric materials (such as, for example, semi-permeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release suppressive ODNs may be administered orally, rectally, parenterally, intracisternally, intravaginally, intraperitoneally, topically (as by powders, ointments, gels, drops or transdermal patch), bucally, or as an oral or nasal spray.

Preparations for administration can be suitably formulated to give controlled release of suppressive ODNs over an extended period of time. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate. For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

Generally, the formulations are prepared by contacting the suppressive ODNs each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise a suppressive ODN, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved. As disclosed herein, therapeutically effective amounts of a suppressive ODN are of use preventing formation of a tumor, treating a tumor, preventing conversion of a benign to a malignant lesion, decreasing the risk of developing a tumor, or preventing metastasis. Administration may begin whenever the suppression or prevention of disease is desired, for example, at a certain age of a subject, or prior to an environmental exposure.

The therapeutically effective amount of suppressive ODN will be dependent on the ODN utilized, the subject being treated, the severity and type of the affliction, and the manner of administration. For example, a therapeutically effective amount of suppressive ODN can vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound (such as the suppressive ODN utilized), the age, weight, sex and physiological condition of the subject.

A therapeutically effective amount of a suppressive ODN can be administered with a therapeutically effective amount of another agent, such as a cytokine, a chemokine, or an immunosuppressive agent. In one example, for the prevention and treatment of cancer, such as melanoma, the suppressive ODN can be used with surgical treatment, or with another therapeutic agents, such as a cytokine, including interleukin-2 (IL-2) or interferon, such as interferon (IFN).

The suppressive ODN can be administered in conjunction with a steroidal anti-inflammatory agent or a non-steroidal anti-inflammatory agents. Steroidal anti-inflammatory agents include glucocorticoids, dexamethasone, prednisone, and hydrocortisone. Non-steroidal anti-inflammatory agents include salicylates (such as Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate. Salicylamide) Arylalkanoic acids (such as Diclofenac, Aceclofenac, Acemethacin, Alclofenac Bromfenac, Etodolac, Indomethacin, Nabumetone, Oxametacin, Proglumetacin, Sulindac, Tolmetin), 2-Arylpropionic acids (such as Ibuprofen, Alminoprofen, Carprofen, Dexibuprofen, Dexketoprofen, Fenbufen, Fenoprofen, Flunoxaprofen, Flurbiprofen, Ibuproxam, Indoprofen, Ketorolac, Loxoprofen, Naproxen, Oxaprozin, Pirprofen, Suprofen, Tiaprofenic acid), N-Arylanthranilic acids (such as Mefenamic acid, Flufenamic acid, Meclofenamic acid, Tolfenamic acid) Pyrazolidine derivatives (such as Phenylbutazone, Ampyrone, Azapropazone, Clofezone, Kebuzone, Metamizole, Mofebutazone, Oxyphenbutazone, Phenazone, Sulfinpyrazone) Oxicams (such as Piroxicam, Droxicam, Lornoxicam, Meloxicam, Tenoxicam or COX-2 inhibitors.

The disclosure is illustrated by the following non-limiting Examples.

EXAMPLES

Example 1

Materials and Methods

The following were used in the studies:
Reagents:
DMBA (7,12, dimethylbenzanthracene
TPA (phorbol 12-tetradecadnoate 13-acetate
Endotoxin-free phosphorothioate ODN were synthesized at the Center for Biologics Evaluation and Research core facility. ODNs were prepared in 80% acetone solution and stored at 4° C. in the refrigerator.

Suppressive ODN A151: (TTAGGG)$_4$ (SEQ ID NO: 1)

Neutral ODN 1612: GCTAGATGTTAGCGT (SEQ ID NO: 29)

CpG ODN 1555: GCTAGACGTTAGCGT (SEQ ID NO: 30)

All chemicals were prepared in acetone solution and stored in the −20° C. freezer.

ODNs were prepared in 80% acetone solution and stored at 4° C. in the refrigerator.

Animals:

Female CD-1 mice (5-6 weeks old) were obtained from the Charles River Laboratories (Frederick, Md.) and acclimatized for 1 week before use. All experiments were conducted under approved animal protocols. Animals were divided into the following groups:

DMBA+TPA (vehicle group)
DMBA+TPA+A151 (suppressive ODN group)
DMBA+TPA+ODN1555 (CpG ODN control group)

Animals were administered 50 μg of CpG ODN 1555 (GCTAGACGTTAGCGT; SEQ ID NO: 30), suppressive ODN A151 (TTAGGG TTAGGGTTAGGGTTAGGG; SEQ ID NO: 1) or control ODN 1612 (GCTAGAGCTTAGGCT; SEQ ID NO: 29)

Protocol for Skin Tumorigenesis (FIG. 1):

Female CD-1 mice were used in a DMBA- and TPA-induced 2-stage skin tumorigenesis protocol (*Int. J. Cancer* 113, 423-433, 2005). The mice were shaved using electric clippers, and the mice with hair cycles in the resting phase were used for tumor studies. In each group, 10 animals were used. Tumor induction was initiated in the skin by a single topical application of DMBA (50 μg) in 100 μl acetone. TPA 2.5 μg in 100 μl acetone was administered 2 weeks after DMBA treatment, and repeated weekly up to the termination of the experiments at 16 weeks. ODN treatment was co-administered with TPA. Animals in both groups were watched for any apparent signs of toxicity, such as weight loss or mortality during the entire period of study. The number and size of skin tumors and weight of each mouse was measured weekly. A lesion was recorded as a papilloma when it reached a diameter of >1 mm and was present for ≥2 consecutive weeks.

Statistical Analysis

Differences in tumor incidence was evaluated by the Wilcoxon rank-sum test and one way ANOVA followed by the Bonferroni-Holm procedure.

Example 2

Results

Figure 2:
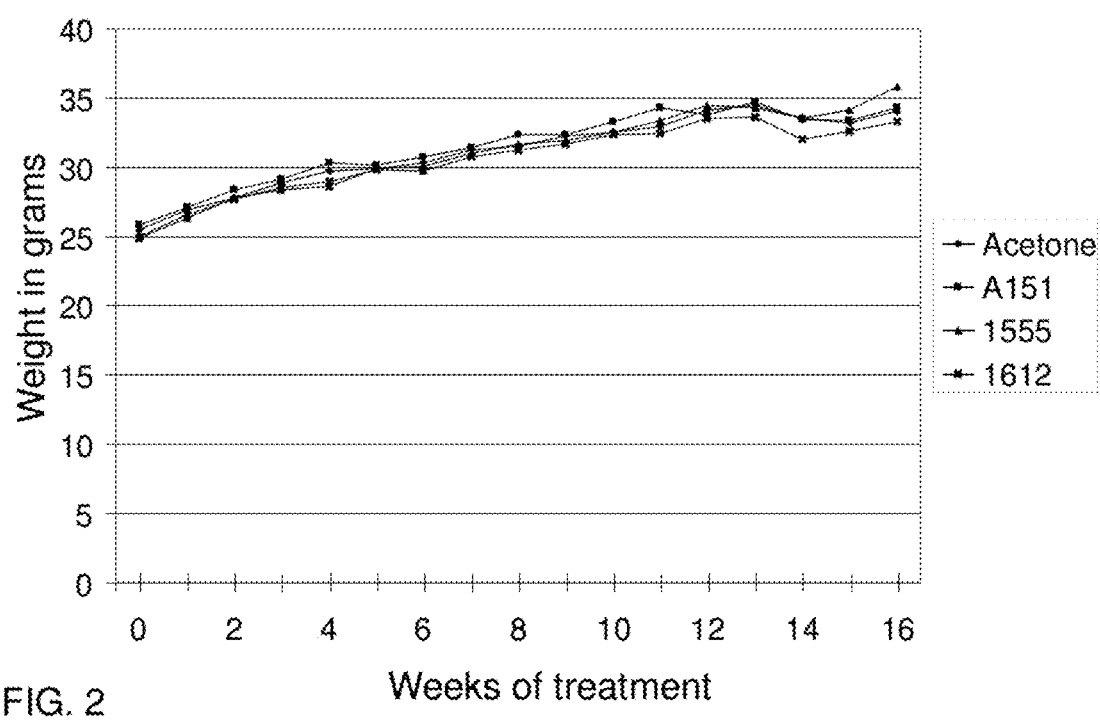
FIG. 2 is a line graph of the body weight of mice treated with ODN A151 (a suppressive ODN), ODN 1612 (a control ODN), vehicle alone or ODN 1555 (an immunostimulatory ODN). The differences were not statistically significant.

Safety of ODN Application:

Changes in weight were used as a general assessment of animal health. As shown in FIG. 2, there were no significant differences in body weight between groups.

Figure 3:
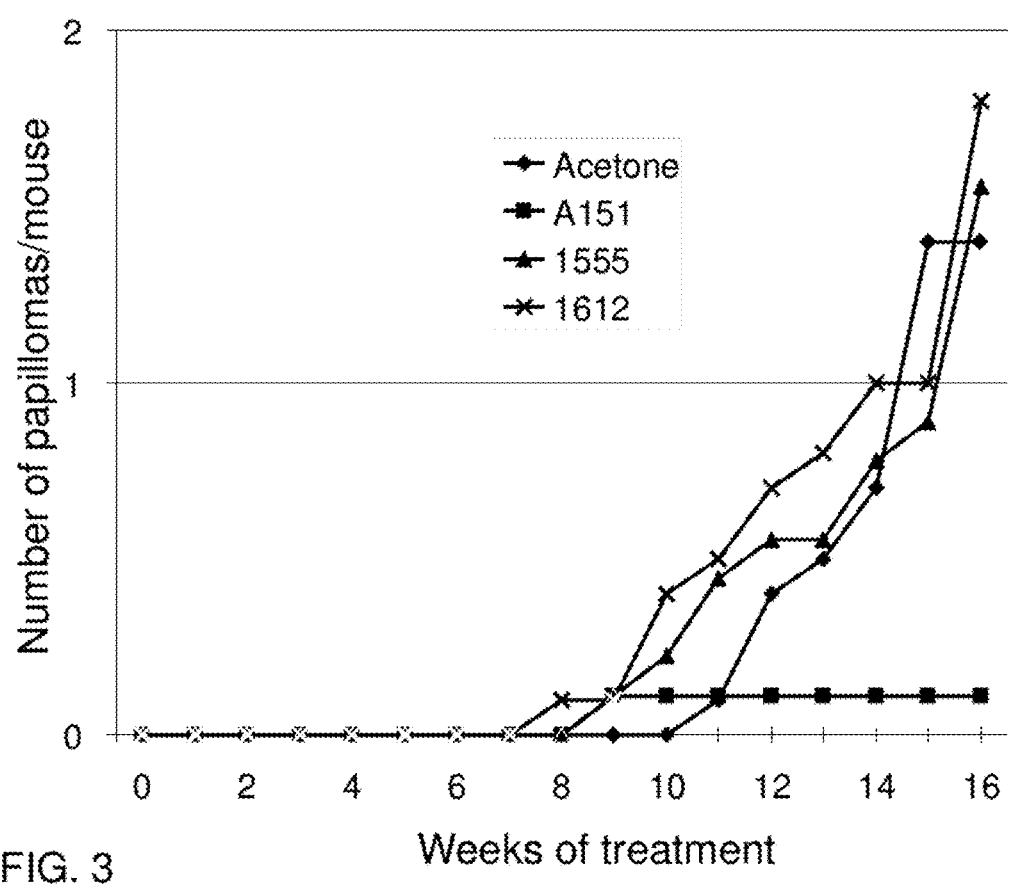
FIG. 3 is a line graph showing the percent of mice with papillomas who were treated with vehicle (acetone) alone, ODN 1612, ODN 1555 or ODN A151. Administration of ODN A151 resulted in a statistically significant decrease in the percentage of mice with papillomas.
Figure 4:
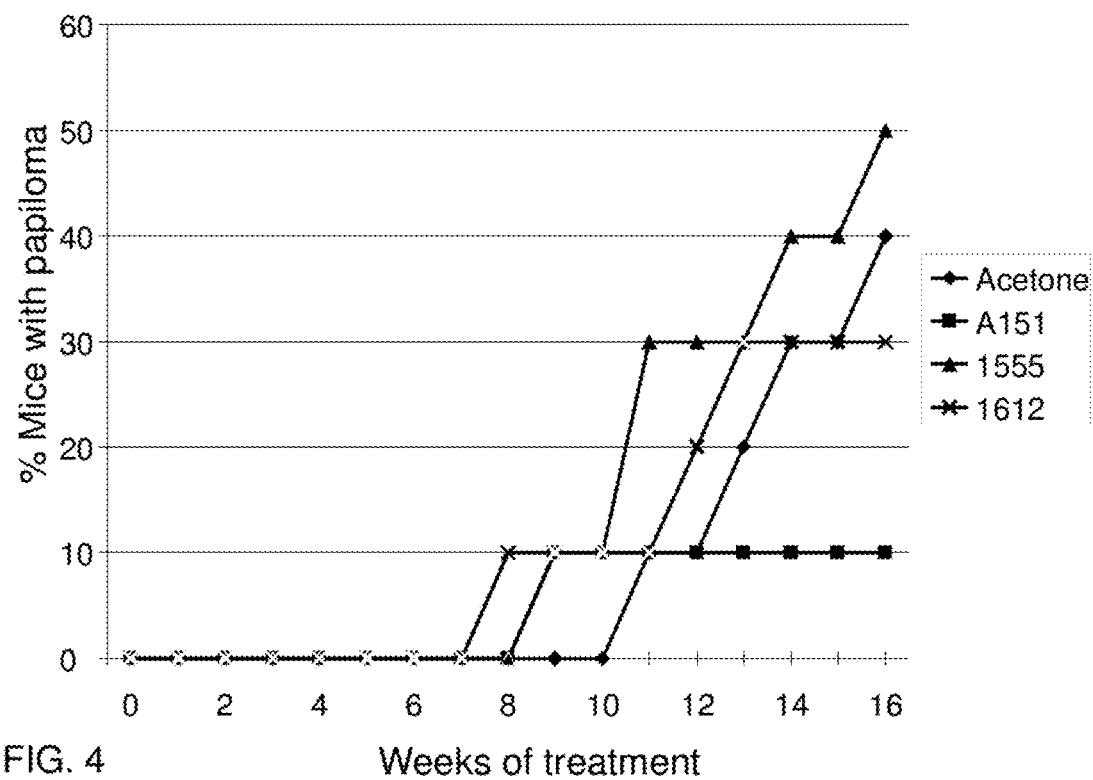
FIG. 4 is a line graph of the total number of papillomas in mice treated with vehicle (acetone) alone, ODN 1612, ODN 1555 or ODN A151. Administration of ODN A151 resulted in a statistically significant decrease in the total number of papillomas.

Inhibitory Effect of Suppressive ODN on TPA-Induced Skin Tumor Promotion:

Topical application of the suppressive ODN A151 to mice treated with DMBA followed by TPA resulted in an inhibition in papilloma development. This inhibition included fewer animals developing papillomas and fewer papillomas per animal (FIGS. 3 and 4). Mice treated with control or CpG ODN developed papillomas significantly more frequently than those treated with suppressive ODN. For example, the A151-treated group had 93.8% fewer papillomas than those treated with control ODN.

Figure 5:
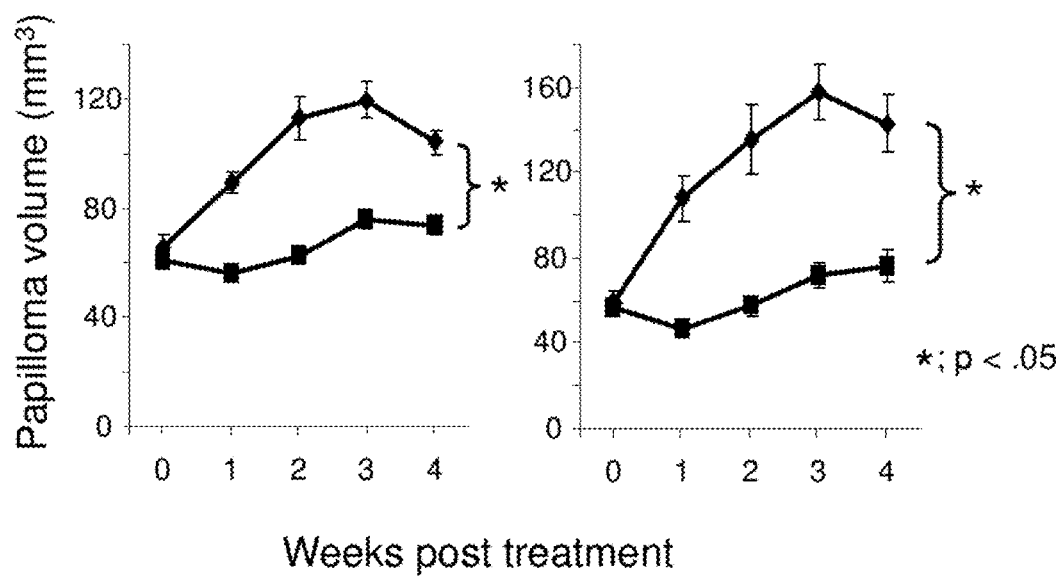
FIG. 5 is a pair of line graphs showing growth of established papillomas in mice treated with suppressive ODN A151. Papillomas were induced in mice by treatment with DMBA and TPA for 16 weeks. The left graph shows treatment of mice in which all papillomas were injected with either ODN 1612 (diamonds) or ODN A151 (squares); the right graph shows treatment of mice in which only half of the papillomas were injected with either ODN 1612 (diamonds) or ODN A151 (squares). The results demonstrate that administration of suppressive ODN A151 results in a statistically significant decrease in growth of established papillomas and that the effect of the suppressive ODN is local rather than systemic.

Inhibitory Effect of Suppressive ODN on Established Papillomas:

To test whether suppressive ODN is capable of inhibiting growth of established papillomas, papillomas were induced by treating mice with DMBA and TPA for 16 weeks and established papillomas were injected with 30 μg of suppressive ODN A151 or control ODN. In one study, all papillomas in each mouse were injected with either ODN A151 or control ODN. In a second study, only half of the papillomas in each mouse were injected with either ODN A151 or control ODN. As shown in FIG. 5, suppressive ODN significantly decreased tumor volume of established papillomas in both studies. In addition, the effect of suppressive ODN on tumor regression is local rather than systemic, a finding that was confirmed by the inability of suppressive ODN to influence papilloma growth when administered intravenously.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

The invention claimed is:

1. A method for preventing or delaying development of a lung tumor in a subject by reducing inflammation in the lung, comprising
selecting a subject at risk for developing a lung tumor, and administering to the subject a therapeutically effective amount of a suppressive oligodeoxynucleotide effective to inhibit inflammation, wherein the suppressive oligodeoxynucleotide is at least about 8 nucleotides in length, forms a G-tetrad, has a CD value of greater than about 2.9, and comprises at least four guanosines,
thereby preventing or delaying development of the lung tumor in the subject.

2. The method of claim 1, wherein the oligodeoxynucleotide has a CD value of greater than about 3.0.

3. The method of claim 1, wherein the oligodeoxynucleotide comprises:
(a) from about 2 to about 4 guanosine-rich sequences;
(b) at least one TTAGGG motif; or
(c) both (a) and (b).

4. The method of claim 3, wherein the oligodeoxynucleotide comprises from about 2 to about 4 TTAGGG motifs.

5. The method of claim 1, wherein the oligodeoxynucleotide comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and combinations of two or more thereof.

6. The method of claim 1, wherein the oligodeoxynucleotide comprises the sequence of SEQ ID NO: 1.

7. The method of claim 1, wherein the tumor is a benign tumor.

8. The method of claim 1, wherein the tumor is a malignant tumor.

9. A method of reducing the risk of a subject to developing a lung tumor by reducing inflammation in the lung, comprising
selecting a subject at risk for developing a lung tumor who has been exposed to a lung tumor carcinogen; and
administering to the subject a therapeutic amount of a suppressive oligodeoxynucleotide effective to inhibit inflammation, wherein the suppressive oligodeoxynucleotide is at least about 8 nucleotides in length, forms a G-tetrad, has a CD value of greater than about 2.9, and comprises at least four guanosines,
thereby reducing the risk of the subject to developing the lung tumor.

10. The method of claim 9, wherein the carcinogen can cause lung cancer.

11. The method of claim 10, wherein the lung cancer is an adenocarcinoma.

12. The method of claim 9, wherein the oligodeoxynucleotide has a CD value of greater than about 3.0.

13. The method of claim 9, wherein the oligodeoxynucleotide comprises:
  (a) from about 2 to about 4 guanosine-rich sequences;
  (b) at least one TTAGGG motif; or
  (c) both (a) and (b).

14. The method of claim 13, wherein the oligodeoxynucleotide comprises from about 2 to about 4 TTAGGG motifs.

15. The method of claim 9, wherein the oligodeoxynucleotide comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and combinations of two or more thereof.

16. The method of claim 9, wherein the oligodeoxynucleotide comprises the sequence of SEQ ID NO: 1.

17. The method of claim 9, wherein the oligodeoxynucleotide has a CD value of greater than about 3.2.

18. The method of claim 9, wherein the subject has been exposed to a carcinogen in cigarette smoke.

19. The method of claim 1, wherein the oligodeoxynucleotide has a CD value of greater than about 3.2.

20. The method of claim 1, wherein the subject at risk for developing a lung tumor has been exposed to a carcinogen in cigarette smoke.

* * * * *

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
ttagggttag ggttagggtt aggg                                         24

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide
```

-continued

```
<400> SEQUENCE: 2
ttagggttag ggttaggg                                             18

<210> SEQ ID NO 3
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 3
ttagggttag gg                                                   12

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
tgggcggttg ggcggttggg cggt                                      24

<210> SEQ ID NO 5
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 5
tgggcggttg ggcggt                                               16

<210> SEQ ID NO 6
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 6
tcaaccttca ttaggg                                               16

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
ttagggttag ggtcaacctt ca                                        22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
tcaaccttca ttagggttag gg                                        22
```

```
<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
gggttagggt tatcaacctt ca                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
tcaaccttca gggttagggt ta                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
gggtgggtgg gtattaccat ta                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
attaccatta gggtgggtgg gt                                              22

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
tgggcggttc aagcttga                                                   18

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
tcaagcttca tgggcggt                                                   18

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 15
gggtgggtgg gtagacgtta cc                                              22

<210> SEQ ID NO 16
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 16 gggggtcaa gcttca                                                      16

<210> SEQ ID NO 17
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 17
tcaagcttca gggggg                                                     16

<210> SEQ ID NO 18
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 18 gggggtcaa cgttca                                                      16

<210> SEQ ID NO 19
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 19
cctcaagctt gagggg                                                     16

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gagcaagctg gaccttccat                                                 20

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
gagcaagctg gtagacgtta g                                               21
```

```
<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gggcaagctg gacctggggg                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ggggaagctg gacctggggg                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gggcaagctg gaccttcggg                                              20

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
ggcaagctgg accttcgggg gg                                           22

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(11)
<223> OTHER INFORMATION: 7-deazaguanine

<400> SEQUENCE: 26
gagcaagctg gaccttccat                                              20

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: 7-deazaguanine
<220> FEATURE:
<221> NAME/KEY: modified_base
<222> LOCATION: (10)..(10)
<223> OTHER INFORMATION: 7-deazaguanine
```

```
<400> SEQUENCE: 27
gagcaagctg gtagacgtta g                                        21

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 7-deazaguanine
<220> FEATURE:
<221> NAME/KEY: modified_base
<222> LOCATION: (10)..(10)
<223> OTHER INFORMATION: 7-deazaguanine

<400> SEQUENCE: 28
gagcaagctg gtagacgtta g                                        21

<210> SEQ ID NO 29
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 29
gctagatgtt agcgt                                               15

<210> SEQ ID NO 30
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 30
gctagacgtt agcgt                                               15
```